United States Patent
Conaway et al.

(10) Patent No.: US 6,858,709 B1
(45) Date of Patent: Feb. 22, 2005

(54) COMPONENT OF VON HIPPEL-LINDAU TUMOR SUPPRESSOR COMPLEX AND SCF UBIQUITIN LIGASE

(75) Inventors: Joan W. Conaway, Kansas City, MO (US); Ronald C. Conaway, Kansas City, MO (US); Takumi Kamura, Fukuoka (JP)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/914,324
(22) PCT Filed: Feb. 25, 2000
(86) PCT No.: PCT/US00/04838

§ 371 (c)(1),
(2), (4) Date: Aug. 22, 2001

(87) PCT Pub. No.: WO00/50445

PCT Pub. Date: Aug. 31, 2000

Related U.S. Application Data

(60) Provisional application No. 60/121,787, filed on Feb. 26, 1999.

(51) Int. Cl.$^7$ ............................ C07K 1/100; C07K 1/00
(52) U.S. Cl. ..................... 530/350; 530/835; 530/828
(58) Field of Search ............................. 530/350, 835, 530/828

(56) References Cited

PUBLICATIONS

Duan et al. (Proc.Natl.Acad.Sci., Jul. 1995, vol. 92, pp. 6459–6463).*
Pause et al. (Proc.Natl.Acad.Sci., Mar. 1997, vol. 94, pp. 2156–2161).*
Ohta, et al., "ROC1, A Homolog of APC11, Represents a Family of Cullin Partners with an Associated Ubiquitin Ligase Activity", Mol. Cell, vol. 3, pp. 535–541, (Apr. 1999).
Alliel, et al., "Testican, A Multidomain Testicular Proteoglycan Resembling Modulators of Cell Social Behavior", Eur. J. Biochem. pp. 214, 347–350 (1993).
Kamura, et al., "RBX1, A Component of the VHL Tumor Suppressor Complex and SCF Ubiquitin Ligase", Science, vol. 284, pp. 657–681, (Apr. 23, 1999).

* cited by examiner

*Primary Examiner*—Gary B. Nickol
(74) *Attorney, Agent, or Firm*—Townsend and Townsend and Crew LLP

(57) ABSTRACT

Rbx1, an evolutionarily conserved Cullin-interacting RING-H2 finger protein, has been discovered. Mammalian Rbx1 has been identified as a component of the CUL2-containing VHL complex. An Rbx1 homolog from *S. cerevisiae* has also been identified as a subunit and activator of the Cdc53-containing SCF$^{Cdc4}$ ubiquitin ligase required for ubiquitination of the cdk inhibitor Sic1 and for the G1/S cell cycle transition in yeast, providing a link between the multiprotein VHL tumor suppressor complex and cellular ubiquitination. The Rbx1 protein acts as a cellular marker useful (1) in detecting a possible predisposition to certain carcinomas, (2) as a molecular target for treating those carcinomas therapeutically. (3) as a target for inhibition by drugs that manipulate the growth of cells, and (4) as a research tool to better understand the various complex mechanisms of cell ubiquitination, binding of certain activator proteins, fibronectin deposition and other aspects of the cellular division process.

12 Claims, 5 Drawing Sheets

A rbx1Δ                               Inviable
rbx1Δ / pGAL-mRbx1 (WT)   viable
rbx1Δ / pGAL-mrbx1 (M3)   Inviable
rbx1Δ / pGAL-mrbx1 (M4)   viable

B

WB: myc-mRbx1   —  -19

WB: Sic1 (yN-19)      -52
                      -37
                      -27

WB: Sic1 (yC-19)      -52
                   1  2

C gal glu

COMPONENT OF VON HIPPEL-LINDAU TUMOR SUPPRESSOR COMPLEX AND SCF UBIQUITIN LIGASE

CROSS REFERENCE TO RELATED APPLICATIONS

This application claims the benefit of and all rights of priority to U.S. Provisional Application Ser. No. 60/121,787, filed Feb. 26, 1999, which is incorporated herein by reference.

TECHNICAL FIELD OF THE INVENTION

The invention relates to a bio-affecting and body treating composition and to a biological diagnostic agent.

BACKGROUND OF THE INVENTION

The von Hippel-Lindau (VHL) tumor suppressor gene on chromosome 3p25.5 is mutated in the majority of sporadic clear cell renal carcinomas and in VHL disease, an autosomal dominant familial cancer syndrome that predisposes affected individuals to a variety of tumors including clear cell renal carcinomas, cerebellar hemangioblastomas and hemangiomas, retinal angiomata, and pheochromocytomas. (Linehan, et al. 1995. "Identification of the von Hippel-Lindau (VHL) gene. Its role in renal cancer," *JAMA* 273:564–570; Gnarra, et al. 1996. "Molecular cloning of the von Hippel-Lindau tumor suppressor gene and its role in renal carcinoma," *Biochim Biophys Acta* 1242;201–210; and Kaelin, W. G. and E. R. Maher. 1998. "The VHL tumor-suppressor gene paradigm," *Trends Genet* 14:423–426). The VHL protein is expressed in most tissues and cell types and appears to perform multiple functions, including general repression of hypoxia-inducible genes (Iliopoulos, et al. 1996. "Negative regulation of hypoxia-inducible genes by the von Hippel-Lindau protein," *Proc Natl Acad Sci USA* 93:10595–10599; Gnarra, et al. 1996. Post-transcriptional regulation of vascular endothelial growth factor mRNA by the product of the VHL tumor suppressor gene," *Proc Natl Acad Sci USA* 93:10589–10594; and Siemeister, et al. 1996. "Reversion of deregulated expression of vascular endothelial growth factor in human renal carcinoma cells by von Hippel-Lindau tumor suppressor protein," *Cancer Res* 56:2299–2301); regulation of p27 protein stability (Pause, et al. 1998. "The von Hippel-Lindau tumor suppressor gene is required for cell cycle exit upon serum withdrawal," *Proc Natl Acad Sci USA* 95:993–998; and Kim, et al. 1999. "Recombinant adenovirus expressing Von Hippel-Lindau-mediated cell cycle arrest is associated with the induction of cyclin-dependent kinase inhibitor p27Kipl," *BBRC* 253:672–677); and regulation of the assembly of extracellular fibronectin matrix (Ohh, et al. 1998. "The von Hippel-Lindau tumor suppressor protein is required for proper assembly of an extracellular fibronectin matrix," *Mol Cell* 1:959–968).

In all cell types examined, the VHL protein is found in a multiprotein complex that includes the ubiquitin-like Elongin B protein, and Elongin C and the cullin CUL2, which share sequence similarity with the Skp1 and Cdc53 components of the Skp1-Cdc53p-F-box protein (SCF) ubiquitin ligase complex, respectively. (Kibel, et al. 1995. "Binding of the von Hippel-Lindau tumor suppressor protein to Elongin B and C," *Science* 269:1444–1446; Duan, et al. 1995. "Inhibition of transcription elongation by the VHL tumor suppressor protein," *Science* 269:1402–1406; Pause, et al. 1997. "The von Hippel-Lindau tumor-suppressor gene product forms a stable complex with human CUL-2, a member of the Cdc53 family of proteins," *Proc Natl Acad Sci USA* 94:2156–2161; and Lonergan, et al. 1998. "Regulation of hypoxia-inducible mRNAs by the von Hippel-Lindau tumor suppressor protein requires binding to complexes containing Elongins B/C and Cul2,"*Mol Cell Biol* 18:732–741). Elongins B and C form a stable subcomplex that interacts with a short BC-box motif in the VHL protein and bridges its interaction with CUL2. (Pause, et al. 1997. *Proc Natl Acad Sci USA* 94:2156–2161; Lonergan, et al. 1998. *Mol Cell Biol* 18:732–741). A large fraction of VHL mutations found in sporadic clear cell renal carcinomas and in VHL kindreds result in mutation or deletion of the BC-box, disruption of the VHL complex, and deregulation of hypoxia-inducible gene expression, p27 protein stability, and bironectin matrix assembly. (Gnarra, et al. 1996. *Biochim Biophys Acta* 1242:201–210; Pause, et al. 1997. *Proc Natl Acad Sci USA* 94:2156–2161; Lonergan, et al. 1998. *Mol Cell Biol* 18:732–741; Ohh, et al. 1998. *Mol Cell* 1:959–968; and Kaelin, W. G. and E. R. Maher. 1998. *Trends Genet* 14:423–426).

Despite information currently available regarding the multiprotein complex that includes the VHL protein, Elongin B, Elongin C, and CUL2, not all components of this complex and the binding relationship of these components to one another have been elucidated. There is a continuing need to characterize yet unknown components of the complex and their interaction with other components to further the understanding of the complex and its relationship to disease.

BRIEF DESCRIPTION OF THE DRAWINGS

FIG. 1A is a schematic showing the various steps used in the purification of the VHL complex, wherein P-cell= phosphocellulose P11.

FIG. 1B is a chromatography of Rbx1 with the VHL complex, wherein VHL=von Hippel-Lindau protein; CUL2=CUL2 protein or cullin; EloB–Elongin B; EloC= Elongin C. Aliquots of column fractions from the MonoQ column were subjected to 12% SDS-polyacrylamide gel electrophoresis, and proteins were detected by silver staining.

FIG. 1C depicts a 5–20% SDS-polyacrylamide gel of sample used for peptide sequencing.

FIG. 3a demonstrates Rbx1 forming complexes with VHL and CUL2 in the presence of Elongin BC. Lysates from Sf21 cells expressing the indicated viruses were immunoprecipitated with anti-FLAG or anti-MYC antibodies, and immunoprecipitated proteins were detected by immunoblotting.

FIG. 3B demonstrates independent association of Rbx1 with Elongin BC, and VHL. Lysates from Sf21 cells expressing the indicated viruses were immunoprecipitated with anti-HPC4, anti-FLAG, or anti-MYC antibodies, and immunoprecipitated proteins were detected by inmnunoblotting.

FIG. 3C demonstrates in vitro binding of recombinant Rbx1, VHL, and Elongin BC. Proteins expressed in and purified from E. coli were mixed together in the combinations indicated, renatured by dilution and dialysis, and immunoprecipitated with anti-HPC4. Immunoprecipitated proteins were detected by immunoblotting with the indicated antibodies.

FIG. 3D demonstrates independent association of Rbx1 with Cul1, Cul2, and Cdc53. Lysates from Sf21 cells expressing the indicated viruses were immunoprecipitated with anti-MYC antibodies, and immunoprecipitated proteins were detected by immunoblotting.

FIG. 4A demonstrates that binding of Rbx1 protein to endogenous yeast Cdc53 correlates with function. The upper panel shows phenotypes of rbx1Δ cells expressing wild type or mutant mammalian Rbx1 (mRbx1) protein. As shown in the lower panel, lysates from cells expressing wild type and mutant manmnalian MYC-Rbx1 proteins in either the rbx1 deletion strain (deleted) or in the parental strain MCY453 (wild type) were subjected to immunoprecipitation with anti-MYC antibodies. Immunoprecipitated proteins were detected by immunoblotting with anti-MYC or anti-Cdc53 antibodies.

FIG. 4B demonstrates that Sic1 protein accumulates in Rbx1-depleted cells. Rbx1Δ/pGAL-mrbx1 (M4) cells were grown to an OD600 of 1 in galactose-containing medium and then shifted into glucose medium. Cells were harvested after 8 hours of growth in glucose, and cell lysates were analyzed by immunoblotting with anti-MYC and two different anti-Sic1 antibodies.

FIG. 4C demonstrates morphological changes associated with Rbx1-depletion. Rbx1Δ/pGAL-mrbx1 (M4) cells were grown in galactose (gal) or for 8 hours after glucose shift (glu) prior to fixation and staining. Nuclear morphology was visualized by DAPI (4,6-diamidino-2-phenylindole) staining. (Panels A and C. DIC; panels B and D, DAPI).

DETAILED DESCRIPTION OF THE INVENTION

Definitions

Figure 1:
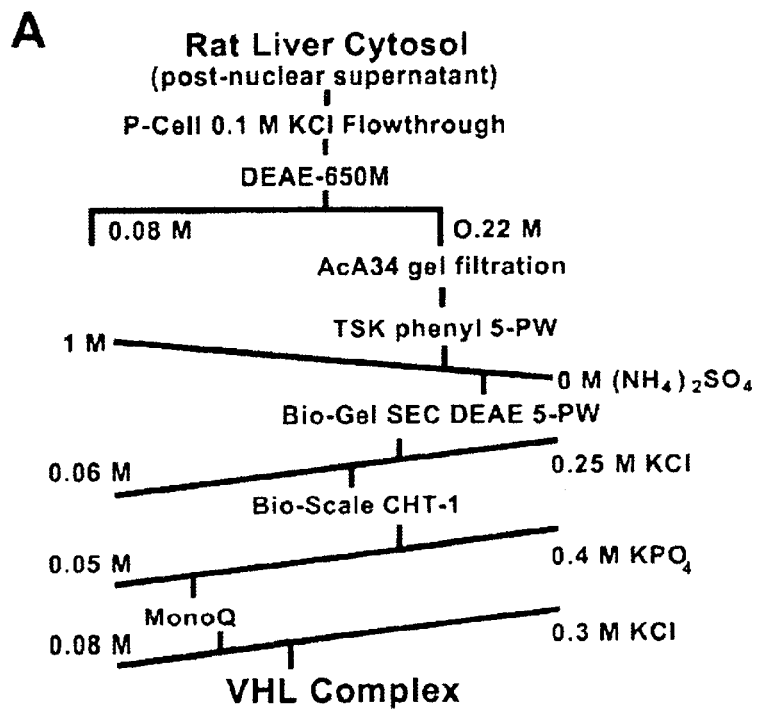
FIGS. 1A–1C describe the co-purification of the VHL complex with Rbx1 from rat liver cytosol.
Figure 1:
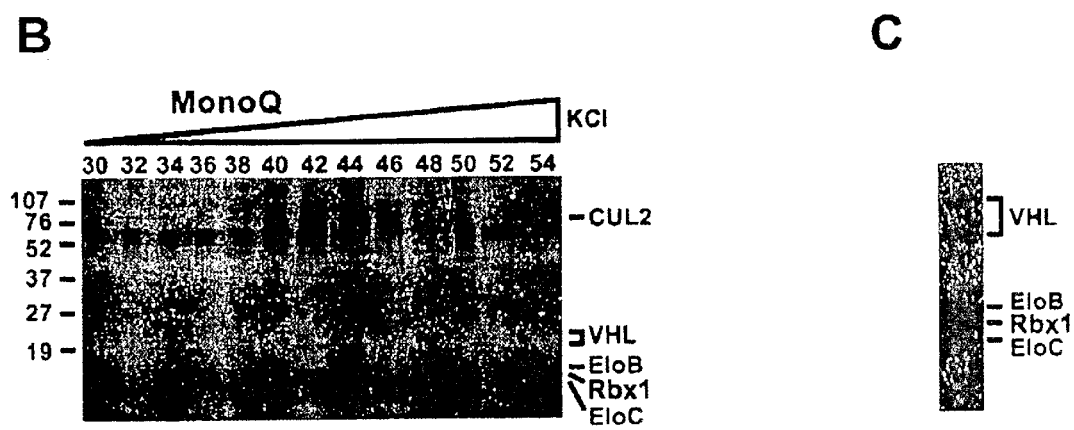

The terms "Ring box protein" and "Rbx1" as used herein refers to proteins that are components of the von Hippel-Lindau tumor suppressor complex. The terms refer to proteins obtained from any eukaryotic species, particularly mammalian species such as bovine, porcine, murine, equine, and human, and from any source whether natural, synthetic, semi-synthetic, or recombinant. The terms encompass polypeptides or proteins having less than the complete amino acid sequence and biologically active variants and gene products.

The term "naturally occurring" as used herein means an endogenous or exogenous protein isolated and purified from animal tissue or cells.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means a protein having structural, regulatory, or biochemical functions of a naturally occurring molecule.

The term "nucleotide sequence" as used herein means a polynucleotide molecule in the form of a separate fragment or as a component of a larger nucleic acid construct that has been derived from DNA or RNA isolated at least once in substantially pure form (ie., free of contaminating endogenous materials) and in a quantity or concentration enabling identification, manipulation, and recovery of its component nucleotide sequences by standard biochemical methods. Such sequences are preferably provided in the form of an open reading frame uninterrupted by internal non-translated sequences, or introns that are typically present in eulkaryotic genes. Sequences of non-translated DNA may be present 5' or 3' from an open reading frame where the same do not interfere with manipulation or expression of the coding region.

The term "nucleic acid molecule" as used herein means RNA or DNA, including cDNA, single or double stranded, and linear or covalently closed molecules. A nucleic acid molecule may also be genornic DNA corresponding to the entire gene or a substantial portion thereof or to fragments and derivatives thereof. The nucleotide sequence may correspond to the naturally occurring nucleotide sequence or may contain single or multiple nucleotide substitutions, deletions and/or additions including fragments thereof. All such variations in the nucleic acid molecule retain the ability to encode a biologically active protein when expressed in the appropriate host or a biologically active fragment thereof The nucleic acid molecule of the present invention may comprise solely the nucleotide sequence encoding a protein or may be part of a larger nucleic acid molecule that comprises the gene for ]extends to the gene for the protein. The non-protein encoding sequences in a larger nucleic acid molecule may include vector, promoter, terminator, enhancer, replication, signal sequences, or non-coding regions of the gene.

The term "variant" as used herein means a polypeptide substantially homologous to a naturally occurring protein but which has an amino acid sequence different from the naturally occurring protein (human, bovine, ovine, porcine, murine, equine, or other eukaryotic species) because of one or more deletions, insertions, derivations, or substitutions. The variant amino acid sequence preferably is at least 40% identical to a naturally occurring amino acid sequence but is most preferably at least 70% identical. Variants may comprise conservatively substituted sequences wherein a given amino acid residue is replaced by a residue having similar physiochemical characteristics. Conservative substitutions are well known in the art and include substitution of one aliphatic residue for another, such as Ile, Val, Leu, or Ala for one another, or substitutions of one polar residue for another, such as between Lys and Arg; Glu and Asp; or Gln and Asn. Conventional procedures and methods can be used for making and using such variants. Other such conservative substitutions such as substitutions of entire regions having similar hydrophobicity characteristics are well known. Naturally occurring variants are also encompassed by the present invention. Examples of such variants are proteins that result from alternate mRNA splicing events or from proteolytic cleavage of the protein that leave the protein biologically active and capable of performing its biological function. Alternate splicing of mRNA may yield a truncated but biologically active protein. Variations attributable to proteolysis include differences in the N- or C-termini upon expression in different types of host cells due to proteolytic removal of one or more terminal amino acids from the protein.

The term "substantially the same" as used herein means nucleic acid or amino acid sequences having sequence variations that do not materially affect the nature of the protein, ie., the structure and/or biological activity of the protein. With particular reference to nucleic acid sequences, the term "substantially the same" is intended to refer to the coding region and to conserved sequences governing expression and refers primarily to degenerate codons encoding the same amino acid or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The term "percent identity" as used herein means comparisons among amino acid sequences as defined in the UWGCG sequence analysis program available from the University of Wisconsin. (Devereaux et al., Nucl. Acids Res. 12: 387–397 (1984)).

This invention is not limited to the particular methodology, protocols, cell lines, vectors, and reagents described because these may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise, e.g. reference to "a host cell" includes a plurality of such host cells.

Because of the degeneracy of the genetic code, a multitude of nucleotide sequences encoding Rbx1 or other Ring box proteins referred to herein may be produced. Some of these sequences will be highly homologous and some will be minimally homologous to the nucleotide sequences of any known and naturally occurring gene. The present invention contemplates each and every possible variation of nucleotide sequence that could be made by selecting combinations based on possible codon choices. These combinations are made in accordance with the standard triplet genetic code as applied to the nucleotide sequence of naturally occurring Rbx1 and all such variations are to be considered as being specifically disclosed.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue of prior invention.

The Invention

The present invention provides isolated and purified biologically active cullin-interacting RING-H2 finger proteins ("Ring box proteins") that are a component of the von Hippel-Lindau tumor suppressor complex and of SCF ubiquitin ligase complexes, nucleic acid molecules that encode Ring box proteins, expression vectors having DNA that encode Ring box proteins, host cells that have been transfected or tnansformed with expression vectors having DNA that encode Ring box proteins, methods for producing recombinant Ring box proteins by culturing host cells that have been transfected or transformed with expression vectors having DNA that encode Ring box proteins, isolated and purified recombinant Ring box proteins, complexes and methods that use Ring box proteins to screen for therapeutic agents, methods for diagnosing the predisposition of a patient to certain carcinomas, methods for treating any of several enumerated carcinomas or augmenting metabolically deficient systems in humans and other animals, and methods for evaluating the effectiveness of a therapeutic treatment for Ring box associated carcinomas. In particular, the present invention provides a new Ring box protein designated Rbx1.

Isolation and Purification of Rbx1

The endogenous VHL complex from rat liver was first purified by the procedures given below and outlined in FIG. 1A. The VHL complex was purified from a post-nuclear supernatant prepared from the livers of 360 male Sprague-Dawley rats and fractionated by $(NH_4)_2 SO_4$ precipitation as described previously. (Conaway, et al. 1996. "Purification of RNA polymerase II general transcription factors from rat liver," Meth Enzymol 273:194–207). Fractions containing the VHL complex were identified by Western blotting using IG32, a monoclonal against the VHL protein. (Kibel, et al. 1995. "Binding of the von Hippel-Lindau tumor suppressor protein to Elongin B and C," Science 269:1444–1446). The 0 to 38% $(NH_4)_2 SO_4$ fraction was resuspended in Buffer A [20 mM Hepes-NaOH (pH 7.9), 0.5 mM EDTA, 1 mM DTT, 10% (v/v) glycerol] containing 0.5 MM PMSF, 10 $\mu$g/ml antipain, and 10 $\mu$g/ml leupeptin and was brought to a conductivity equivalent to that of Buffer A containing 100 mM KCl by a 3 hour dialysis against Buffer A containing 0.5 mM PMSF and dilution with the same buffer. The dialysate was centrifuged for 30 min at 28,000×g, and the supernatant was gently mixed for~45 minutes with 800 ml of phosphocellulose (P11, Whatnan) preequlibrated in Buffer A containing 100 Mm M KCl and 0.5 mM PMSF. The slurry was then filtered at 500 ml/hr in a 10.5-cm diameter column. The phosphocellulose flow through fraction was gently mixed for~45 minutes with 250 ml Toyopearl DEAE-650 M (TosoHaas) pre-equilibrated in Buffer C [40 mM Tris-HCl (pH 7.9), 0.5 mM EDTA, 1 M DTT, and 10% (v/v) glycerol] containing 80 mM KCl. The slurry was filtered at 150 ml/hr in a 5.0-cm diameter column and then washed at the same flow rate with Buffer C containing 80 mM KCl. The column was eluted stepwise at 250 ml/hr with Buffer A containing 220 mM KCl, and 50 ml fractions were collected. Fractions containing the VHL protein were concentrated by 0.3 mg/ml $(NH_4)_2 SO_4$ precipitation, resuspended in 10 ml of Buffer A containing 10 $\mu$g/ml antipain and 10 $\mu$g/ml leupeptin, and dialyzed against Buffer A containing 300 mM KCl to a conductivity equivalent to that of Buffer A containing 500 mM $(NH_4)_2SO_4$. Following centrifugation for 15 min at 12,000×g, the resulting supernatant was applied at 20 ml/hr to a 500 ml, 2.6-cm diameter Ultrogel AcA 34 gel filtration column (IBF Biotechnics) pre-equilibrated in Buffer A containing 400 mM KCl. The column was eluted at 20 ml/hr, and 10 ml fractions were collected. Fractions containing the VHL protein, which eluted with an apparent native molecular mass between 330 kDa and 200 kDa, were diluted with an equal volume of Buffer E [40 mM Hepes-NaOH (pH 7.9), 0.1 mM EDTA, 1 mM DTT, and 10% (v/v) glycerol] containing 2.0 M $(NH_4)_2 SO_4$. Following centrifugation for 20 min at 60,000×g, the resulting supernatant was applied to a Spherogel TSK phenyl 5-PW column (21.5-×150-mm, Beckman Instruments) pre-equilibrated in Buffer E containing 1.0 M $(NH_4)_2SO_4$. The column was eluted at 5 ml/min with a 250 ml linear-gradient from 1.0 M $(NH_4)_2 SO_4$ in Buffer E to Buffer E, and 5 ml fractions were collected. Fractions containing the VHL protein, which eluted between 170 mM and 80 mM $(NH_4)_2SO_4$, were pooled and dialyzed against Buffer C to a conductivity equivalent to that of Buffer C containing 60 mM KCl. Following centrifugation for 20 min at 60,000×g, the resulting supernatant was applied to a BioGel SEC DEAE 5-PW column (7.5-×75-mm, Bio-Rad) pre-equilibrated in Buffer C containing 60 mM KCl. The column was eluted at 0.8 mu/min with a 40 ml linear gradient from 60 mM to 250 mM KCl in Buffer C, and 0.7 ml fractions were collected. Fractions containing the VHL protein, which eluted between 120 mM and 140 mM KCl, were pooled and brought to 5 mM potassium phosphate. Following centrifilgation for 20 min at 60,000×g, the resulting supernatant was applied to a crystalline hydroxylapatite Bio-Scale CHT-I column (7-×52-mm, Bio-Rad) pre-equilibrated in Buffer P [5 mM potassium phosphate (pH 7.6), 0.1 mM EDTA, 1 mM DTT, and 10% (v/v) glycerol]. The column was eluted at 0.6 ml/min with a 24 ml linear gradient from 50 mM to 400 mM potassium phosphate (pH 7.6) in Buffer P, and 0.3 ml fractions were collected. Fractions containing the VHL protein, which eluted between 50 mM and 80 mM potassium phosphate, were pooled and diluted with Buffer C containing 50 mM KCl to a conductivity equivalent to that of Buffer C in 80 mM KCl. Following centrifugation for 20 min at 60,000×g, the resulting supernatant was applied to a MonoQ column (5-×50-mm, Phanmacia) preequilibrated in Buffer C containing 80 mM KCl. The column was eluted at 0.4 ml/min with a 12 ml linear gradient from 80 mM to 300 mM KCl in Buffer C, and 0.2 ml fractions were collected. Fractions containing the VHL protein eluted between 180 mM and 200 mM KCl.

As shown in FIGS. 1B and 1C, greater than 90% of the detectable VHL protein in liver homogenates copurified with CUL2, Elongin B, Elongin C, and a small polypeptide with an apparent molecular mass of −16 kDa The identities of the VHL, CTL2, Elongin B, and Elongin C potypeptides were confirmed by Western blotting and/or peptide sequencing. On-line ion trap HPLC/MS/MS peptide sequencing using the method described below (Eng, et al. 1994. *J Am Soc Mass Spectrom* 5:976 and Chittum et al. 1998. *Biochemisty* 37:10866) of the −16 kDa protein excised from the SDS polyacrylamide gel shown in FIG. 1C revealed that it was a novel RING-H2 finger protein, designated "Rbx1" or "Ringbox protein."

Sequencing of Rbx1

Figure 2:
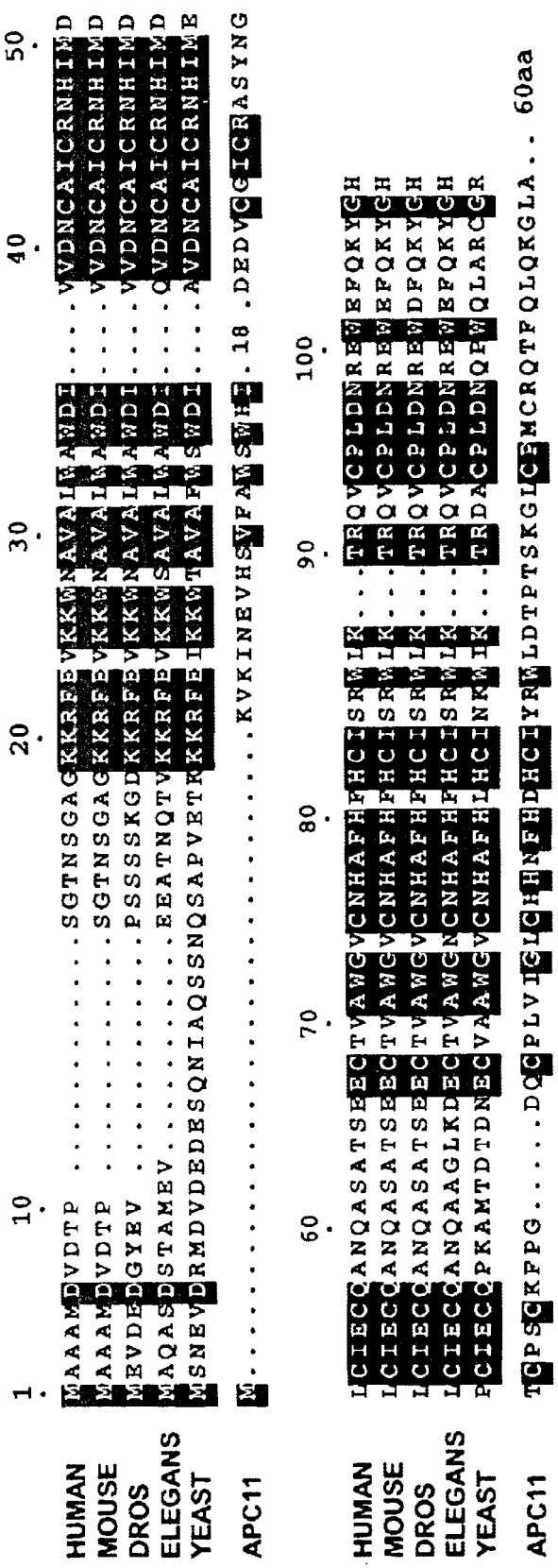
FIG. 2 is a chart showing the alignment of predicted Rbx1 protein sequences from human (SEQ ID NO:1), mouse (SEQ ID NO:1), *Drosophila melanogaster* (SEQ ID NO:6), *Caenorhabditis elegans* (SEQ ID NO:7), and *Saccharomyces cerevisiae* (SEQ ID NO:2) with APC11 from *S. cerevisiae* (SEQ ID NOS:8 and 9), wherein DROS=*Drosophila melanogaste*; ELEGANS=*Caenorhabditis elegans*; and YEAST=*Saccharomyces cerevisiae*. The alignment was generated using the MACAW program. (Schuler, et al. 1991. "A workbench for multiple alignment construction and analysis," *Proteins; Struct Funct Genet* 9:180–190). Dark shading indicates positions of identity between Rbx1 proteins from different species and positions of identity between the Rbx1 and APC11 proteins. Grey shading indicates positions of similaiy.

The VHL tumor suppressor complex was fractionated by 13% SDS-polyacrylarnide gel electrophoresis. Proteins were visualized by staining with Coomassie blue, excised, and subjected to in-gel reduction, S-carboxyamidomethylation, and tryptic digestion. Using 10% of the digestion mixture, peptide sequences were determined in a single run by microcapillary reversed-phase chromatography coupled to the electrospray ionization source of a quadrupole ion trap mass spectrometer (Finnigan LCQ). The ion trap's online data-dependent scans allowed the automatic acquisition of high resolution spectra to determine charge state and exact mass, and tandem mass spectrometry spectra for sequence information. The relative collision energy was 35% AND ISOLATION WIDTH WAS 2.5 Dalton. Searches of the EST database performed using TLASTIN algorithm identified human and mouse ESTs that encoded the peptide sequences NHIMDLCIECQAN (SEQ ID NO:10), QVCPLDNREWEFQK (SEQ ID NO:11), WNAVAL (SEQ ID NO:12) and WLK which were determined by ion trap mass spectrometry of the 16 kDa polypeptide that copurified with the VHL complex. The identification was facilitated with the algorithm SEQUEST (Eng, et al. 1994. *J Am Soc Mass Spectrom* 5:976) and by programs developed in the Harvard Microchemistry Facility (Chittum et al. 1998. *Biochemistry* 37:10866). I.M.A.G.E. Consortium CDNA colonies ("I.M.A.G.E. Consortium: an integrated molecular analysis of genomes and their expression," *Genomics* 33:151–152) encoding the complete 108 amino acid long ORFs of human (H71993) and mouse (W66989 and AA260889) Rbx1 were obtained from Research Genetics, Huntsville, Ala., and the nucleotide sequences of both strands were determined. Human and mouse cDNAs encoded identical polypeptides of 108 amino acids. The amino acid sequence for human and mouse Rbx1 is shown in FIG. 2 and in SEQ ID NO:1. The nucleotide sequence for the human Rbx1 DNA is shown in nucleotides 7–333 or SEQ ID NO:3 and the nucleotide sequence for the murine Rbx1 DNA is shown in nucleotides 18–344 or SEQ ID NO:5, inclusive of the stop codon. Nucleotides 1–6 and 1017 are 5' untranslated regions, respectively and 334–508 and 345–504 are 3' untranslated regions, respectively.

As shown in FIG. 2, Rbx1 is highly homologous to *D. melanogaster* ORF 115C2.11, *C. elegans* ORF ZK287.5, and *S. cerevisiae* ORF YOL133w. The amino acid sequence for *Saccharomyces cerevisiae* Rbx1 is shown in SEQ ID NO:2 and the nucleotide sequence for the *Saccharomyces cerevisiae* Rbx1 DNA is shown in nucleotides 4–369 of SEQ ID NO:4, inclusive of the stop codon. Comparison of the deduced amino acid sequences demonstrates that the proteins are highly homologous with about an 80 percent identity and that the proteins are substantially the same. In addition, Rbx1 exhibits significant sequence similarity with *Saccharomyces cerevisiae* Anaphase-Promoting Complex subunit APC11 (Zachariae, et al. 1998. "Mass spectrometric analysis of the anaphase-promoting complex from yeast: Identification of a subunit related to cullins," *Science* 279:1216–1219).

Because of the degeneracy of the genetic code, a DNA sequence may vary from that shown in SEQ ID NO:3 and still encode a Rbx1 protein having the amino acid sequence shown in SEQ ID NO:1. Such variant DNA sequences may result from silent mutations, e.g., occurring during PCR amplification, or may be the product of deliberate mutagenesis of a native sequence. The invention, therefore, provides equivalent isolated DNA sequences encoding biologically active Rbx1 selected from: (a) the coding region of a native Rbx1 gene; (b) cDNA comprising the nucleotide sequence presented in SEQ ID NO:3; (c) DNA capable of hybridization to the native Rbx1 gene under moderately stringent conditions and which encodes biologically active Rbx1; and (d) DNA which is degenerate as a result of the genetic code to a DNA defined in (a), (b), or (c) and which encodes biologically active Rbx1. Rbx1 encoded by such DNA equivalent sequences are encompassed by the invention.

Recombinant Expression for Rbx1

Isolated and purified recombinant Rbx1 is provided according to the present invention by incorporating the corresponding DNA into expression vectors and expressing the DNA in a suitable host cell to produce the protein.

Expression Vectors

Recombinant expression vectors containing a nucleic acid sequence encoding the protein can be prepared using well known techniques. The expression vectors include a DNA sequence operably linked to suitable transcriptional or translational regulatory nucleotide sequences such as those derived from mammalian, microbial, viral, or insect genes. Examples of regulatory sequences include transcriptional promoters, operators, enhancers, mRNA ribosomal binding sites, and appropriate sequences which control transcripion and translation initiation and termination. Nucleotide sequences are "operably linked" when the regulatory sequence functionally relates to the DNA sequence for the appropriate protein. Thus, a promoter nucleotide sequence is operably linked to a Rbx1 DNA sequence if the promoter nucleotide sequence controls the transcription of the appropriate DNA sequence.

The ability to replicate in the desired host cells, usually conferred by an origin of replication and a selection gene by which transformants are identified, may additionally be incorporated into the expression vector.

In addition, sequences encoding appropriate signal peptides that are not naturally associated with Rbx1 can be incorporated into expression vectors. For example, a DNA sequence for a signal peptide (secretory leader) may be fused in-frame to the protein sequence so that the protein is initially translated as a fusion protein comprising the signal peptide. A signal peptide that is functional in the intended host cells enhances extracellular secretion of the appropriate polypeptide. The signal peptide may be cleaved from the polypeptide upon secretion of protein from the cell

Host Cells

Suitable host cells for expression of Rbx1 include prokaryotes, yeast, archae, and other eukaryotic cells. Appropriate cloning and expression vectors for use with bacterial, fungal, yeast, and mammalian cellular hosts are well known in the art, e.g., Pouwels et al. Cloning Vectors: A Laboratory Manual, Elsevier, N.Y. (1985). The vector may be a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells. Cell-free translation systems could also be employed to produce the protein using RNAs derived from the present DNA constructs.

Prokaryotes useful as host cells in the present invention include grain negative or gram positive organisms such as *E. coli* or Bacilli. In a prokaryotic host cell, a polypeptide may include a N-terminal methionine residue to facilitate expression of the recombinant polypeptide in the prokaryotic host cell. The N-termiinal Met may be cleaved from the expressed recombinant Rbx1 polypeptide. Promoter sequences commonly used for recombinant prokaryotic host cell expression vectors include β-lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, pKK223-3 (Pharrmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, F. W., *J. Mol. Biol.* 219: 37 (1991); Schoepfer, R. *Gene* 124: 83 (1993)).

Promoter sequences commonly used for recombinant prokaryotic host cell expression vectors include T7, (Rosenberg, A. H., Lade, B. N., Chui, D-S., Lin, S-W., Dunn, J. J., and Studier, F. W. (1987) *Gene* (Amst.) 56, 125–135), β-lactamase (penicillinase), lactose promoter system (Chang et al., *Nature* 275:615, (1978); and Goeddel et al., *Nature* 281:544, (1979)), tryptophan (trp) promoter system (Goeddel et al., *Nucl. Acids Res.* 8:4057, (1980)), and tac promoter (Maniatis, Molecular Cloning: A Laboratory Manual, Cold Spring Harbor Laboratory, p. 412 (1982)).

Yeasts useful as host cells in the present invention include those from the genus Saccharomyces, Pichia, K. Actmomycetes and Kluyveromyces. Yeast vectors will often contain an origin of replication sequence from a 2 $\mu$ yeast plasmid, an autonomously replicating sequence (ARS), a promoter region, sequences for polyadenylafion, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, (1980)) or other glycolytic enzymes (Holland et al., Biochem. 17:4900, (1978)) such as enolase, glyceraldehyde-3-phosphate dehydrogenase, hexolinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., *Gene*, 107:285–195 (1991). Other suitable promoters and vectors for yeast and yeast transformation protocols are well known in the art.

Yeast transformation protocols are known to those of skill in the art. One such protocol is described by Hinnen et al., *Proc Natl Acad Sci USA*, 75:1929 (1978). The Hinnen protocol selects for Trp.sup.+transformants in a selective medium, wherein the selective medium consists of 0.67% yeast nitrogen base, 0.5% casamino acids, 2% glucose, 10 $\mu$g/ml adenine, and 20 $\mu$g/ml uracil.

Mammalian or insect host cell culture systems well known in the art could also be employed to express recombinant Rbx1, e.g., Baculovirus systems for production of heterologous proteins in insect cells (Luckow and Summers, *Bio/Technology* 6:47 (1988)) or Chinese hamster ovary (CHO) cells for mammalian expression may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

Rbx1 and other Ring box proteins may, when beneficial, be expressed as a fusion protein that has the Ring box protein attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the protein. Preferred fusion segments include, but are not limited to, glutathione-S-transferase, β-galactosidase, a poly-histidine segment capable of binding to a divalent metal ion, and maltose binding protein.

Expression and Recovery

According to the present invention, isolated and purified Rbx1 may be produced by the recombinant expression systems described above. The method comprises culturing a host cell transformed with an expression vector comprising a DNA sequence that encodes the protein under conditions sufficient to promote expression of the protein. The protein is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. When expression systems that secrete the recombinant protein are employed, the culture medium first may be concentrated. Following the concentration step, the concentrate can be applied to a purification matrix such as a gel filtration medium. Alternatively, an anion exchange resin can be employed, e.g., a matrix or substrate having pendant diethylaminoethyl (DEAE) groups. The matrices can be acrylamide, agarose, dextran, cellulose, or other types commonly employed in protein purification. Also, a cation exchange step can be employed. Suitable cation exchangers include various insoluble matrices comprising sulfopropyl or carboxymethyl groups. Further, one or more reversed-phase high performance liquid chromatography (RP-HPLC) steps employing hydrophobic RP-HPLC media (e.g., silica gel having pendant methyl or other aliphatic groups), ion exchange-HPLC (e.g., silica gel having pendant DEAE or sulfopropyl (SP) groups), or hydrophobic interaction-HPLC (e.g., silica gel having pendant phenyl, butyl, or other hydrophobic groups) can be employed to further purify the protein. Some or all of the foregoing purification steps, in various combinations, are well known in the art and can be employed to provide an isolated and purified recombinant protein.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification, or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

In another aspect, the present invention provides a protein complex useful for screening for potential therapeutic agents that would interfere with or augment Rbx1-dependent stimulation of addition of ubiquitin or a ubiquitin-like protein to any substrate targeted for modification by SCF complexes. The complex contains a cofactor protein and one or more proteins selected from the group consisting of a cullin protein, a substrate recognition protein, and a linker protein. Additional components, e.g., ATP, may be added to the solution or composition: containing the complex to facilitate complex formation and utilization.

In a preferred embodiment, the complex is a ubiquitin ligase protein complex that contains cullin proteins; substrate recognition proteins; linker proteins; and cofactor proteins. The complex preferably has one protein from each group but can have more that one protein from each group if required or preferred. Preferably, the complex is formed from the proteins but the solution or compositions containing the complex may contain additional components if needed to facilitate complex formation and utilization. For example, solutions or compositions containing the complex can comprise various combinations of (1) Skp1, Elongin C, or other linker protein; (2) β-TRCP, Cdc4, Grr1, or other F-box substrate recognition protein or VHL or other Elongin C-Binding substrate recognition protein; (3) CUL1, Cdc53, CUL2, or other cullin protein; (4) Cdc34, UBC5C, or another E2 ubiquitin conjugating enzyme; (5) phosphorylated or other appropriately modified substrate; (6) E1 ubiquitin activating enzyme; (7) ATP; and (8) ubiquitin, GST-ubiquitin, GST-Ubiquitin$^{RA}$, ubiquitin derivatives, or a ubiquitin-like protein such as SUMO, NEDD8, or Rub 1.

Preferably, the complex is a ubiquitin ligase protein complex that contains a cullin protein, a substrate recognition protein, a linker protein, and a cofactor protein. Most preferably, the complex is an isolated and purified ubiquitin ligase protein complex comprising such proteins.

Generally, the cullin proteins of the present invention are proteins selected from the group consisting of Cdc53, Cullin 1 (CUL1), Cullin 2 (CUL2), Cullin 3 (CUL3), Cullin 4A (CUL4A), Cullin 4B (CUL4B), and Cullin 5 (CUL5), preferably CUL1 or CUL2. The substrate recognition proteins are selected from the group consisting of F-box proteins such as β-TRCP (HOS), Cdc4, Grr1, and other members of this protein family and VHL and other Elongin C binding proteins, preferably F-box proteins or VHL. The linker proteins are selected from the group consisting of Skp1 or Elongin C. Many such cullin, substrate recognition, and linker proteins are known in the art and can be used in the present invention. The cofactor proteins are the Ring box proteins of the present invention, preferably Rbx 1.

Figure 5:
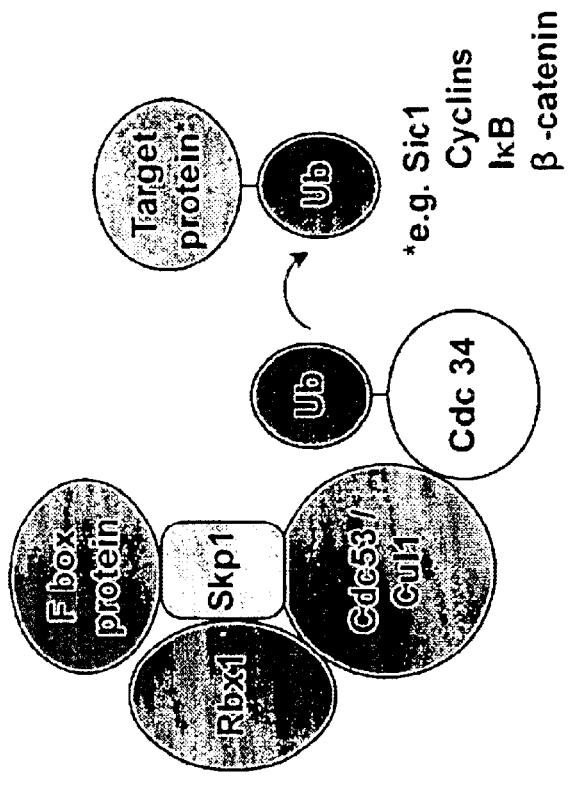
FIG. 5 shows a diagram of a SCF ubiquitin ligase complex and a VHL ubiquitin ligase complex and illustrates the ubiquitin ligases of the present invention.
Figure 5:
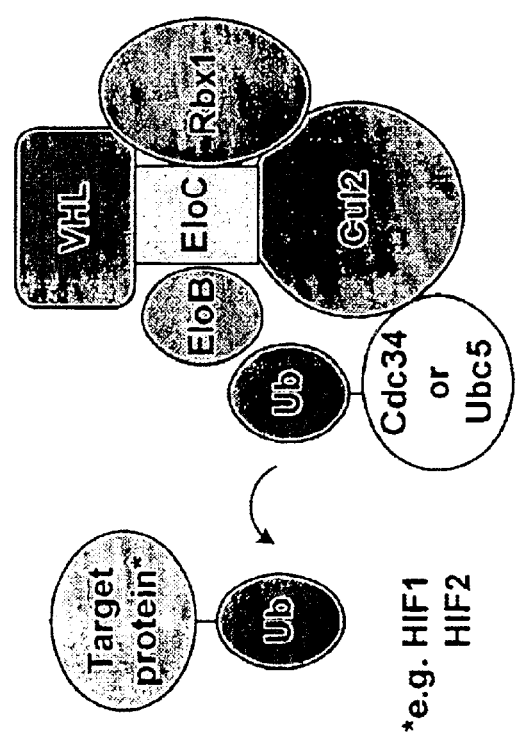

FIG. 5 shows a diagram of SCF and VHL ubiquitin ligase complexes illustrating the ubiquitin ligases of the present invention. The cullin protein is Cdc53/Cul1 in the SCF complex and CUL2 in the VHL complex, the substrate recognition protein is a F-box protein in the SCF complex and the VHL protein in the VHL complex, and the linker protein is Skp1 in the SCF complex and Elongin C in the VHL complex. The VHL complex also contains Elongin B. The cofactor protein Rbx1 binds to the other proteins and activates the ubiquitin ligase. The SCF ubiquitin ligase targets such substrate proteins as Sic1, cyclins, β-catenin, NF-κB inhibitors such as IκBα, and the like, and VHL ubiquitin ligase complex targets such substrate proteins as hypoxia-inducible factor 1 (HIF1) and hypoxia-inducible factor 2 (HIF2)

The present invention also provides methods for screening for potential therapeutic agents that would interfere with or augment Rbx1-dependent stimulation of addition of ubiquitin or a ubiquitin-like protein to any substrate including those targeted for modification by SCF of VHL-containing complexes. The methods require forming a complex in vitro that contains a cofactor protein and one or more proteins selected from the group consisting of a cullin protein, a substrate recognition protein, and a linker protein; adding a test compound to interact with the complex; and determining if the complex remains intact or is disrupted by the compound. If the complex is disrupted, the compound is likely to be a therapeutic agent useful for the treatment of the corresponding disease, e.g., cancer or inflammatory disease. For example, a complex can be formed in vitro between a Cdc53 and Rbx1. A test compound can be added to interact with the complex. An assay, e.g., SDS-PAGE and immunoblotting or other known techniques, can be conducted to determine if the complex remains intact or is disrupted. SCF ubiquitin ligases control the stability of proteins including but not limited to cyclins and cyclin dependent kinase inhibitors, which regulate the cell cycle, and IκB, which regulates inflammatory processes. If the complex is disrupted, the compound is a likely candidate for an anti-cancer agent or an anti-inflammatory drug.

Preferably, the complex used in the methods is the ubiquitin ligase protein complex described herein, most preferably an isolated and purified ubiquitin ligase protein complex.

In similar assays, Rbx1 can be used to screen for agents which augment or inhibit the activity of other Cullin-containing ubiquitin ligases and of the VHL complex controlling the conjugation of ubiquitin or ubiquitin-like proteins to various sets of target proteins. The hypoxia-inducible transcription factor HIF1α is a likely target for ubiquitination by the VHL complex (Maxwell et al "The tumor suppressor protein VHL targets hypoxi-inducible factors for oxygen-dependent proteolysis" *Nature* 399:271, 1999). Hypoxia-inducible transcription factors regulate the expression of hypoxia inducible genes including vascular endothelial growth factor, which controls normal vascularization as well as vascularization of tumors. Hence, compounds that disrupt or interfere with the function of the VHL complex are likely candidates for anticancer drugs or for drugs that promote vascularization.

In another aspect, the present invention provides methods for diagnosing the predisposition of a patient to certain carcinomas. The invention is based upon the discovery that the absence of VHL-associated proteins, i.e., Ring box proteins such as Rbx1, from certain patient tissues or body fluids indicates that the patient is predisposed to certain carcinomas. The method comprises collecting a tissue or body fluid sample from a patient, analyzing the tissue or body fluid for the quantity of Ring box protein in the tissue, and predicting the predisposition of the patient to certain carcinomas based upon the amount of Ring box protein in the tissue or body fluid. Specifically, determination of Rbx1 protein levels in certain tissues permits specific and early, preferably before metastases occur, detection of carcinomas in the patient. Carcinomas that can be diagnosed using the present method include, but are not limited to, clear cell renal carcinoma.

In another aspect, the present invention provides methods for treating any of several enumerated Ring box protein associated carcinomas or augmenting metabolically deficient systems (e.g., fibronectin deposition) in humans and other animals. One method comprises administering a therapeutically effective amount of a compound that enhances or augments in vivo the expression of the target Rbx1 gene and enhances the in vivo the expression of the Ring box protein to a patient diagnosed as having a Ring box protein associated carcinoma or cellular deficienciey and having been diagnosed as deficient in Ring box protein, preferably Rbx1. In a preferred embodiment, the compound is a nucleobase containing a sequence of the nucleic acid sequence encoding the Ring box protein. After administration, the nucleic acid sequence is activated to produce the Ring box protein and increase the amount of the Ring box protein in the cell. Increasing the amount of Ring box protein increases the activity of VHL tumor suppressor activity, ubiquitination, fibronectin deposition, and similar activities. Another method comprises administering a therapeutically effective amount of a Ring box protein to a patient diagnosed as having a Ring box protein associated carcinoma or cellular deficiency and having been diagnosed as deficient in Ring box protein, preferably Rbx1. Carcinomas that can treated using the present method include, but are not limited to, clear cell renal carcinoma.

In another aspect, the present invention provides methods for evaluating the effectiveness of a therapeutic treatment for Ring box associated carcinomas. The method comprises collecting a tissue or body fluid sample from a patient suffering from a Ring box associated carcinomra and having been subjected to a therapeutic treatment for such carcinoma, determining the amount of Ring box protein in the tissue or body fluid sample, and comparing the determined amount or Ring box protein to a standard indicative of normal Ring box protein levels. The standard can be averages of Ring box protein levels for normal patients but preferably is the level of Ring box protein for the patient being treated before the treatment began. Elevated levels of Ring box protein compared to the standard indicates that the treatment is effective.

EXAMPLE 1

Use of Rbx1 with $SCF^{Cdc4}$ in In Vitro Sic1 Ubiquitination Assay

Rbx1 can be used as a research tool to better understand various complex mechanisms of cell ubiquitination. To test directly the role of Rbx1 in $SCF^{Cdc4}$ function, a standard in vitro Sic1 ubiquitination assay that is dependent upon Sic1 phosphorylation and the E2 Cdc4 was employed. (Skowyra, et al. 1997. *Cell* 91:209). $SCF^{Cdc4}$ components were co-expressed in insect cells in the presence or absence of mammalian or yeast Rbx1, and complexes were immunopurified through either MYC-tagged Cdc53(MYC-Cdc53) or FLAG-tagged Skp1 (FLAG-Skp1) subunits. Immunopurified $SCF^{Cdc4}$ complexes were supplemented with phosphorylated Sic1, Cdc4, E1 ubiquitin activating enzyme, ATP, and $GST-Ub^{RA}$ prior to analysis of Sic1 conjugates by immunoblotting. $GST-Ub^{RA}$ forms polyubiquitinated products only poorly, so Sic1 conjugates are integrated into a ladder of bands differing by ~35 kd, the size of $GST-Ub^{RA}$. Under the reaction conditions used, low but detectable amounts of $Sic1-GST-Ub^{RA}$ conjugates were produced by the $SCF^{Cdc4}$ complex after a 60 minute reaction. In the presence of either yeast or mammalian Rbx1, the accumulation of $Sic1-GST-Ub^{RA}$ conjugates was dramaticaly increased after 20 minutes, and substantial amounts of higher molecular mass conjugates accumulated after 60 minutes. A large fraction of phosphorylated Sic1 was converted to Sic1-GST-Ub$^{RA}$ conjugates when reactions included either the anti-Cdc53 or anti-FLAG-Skp1 immune complexes; e.g., >95% or Sic1 was converted to conjugates in reactions containing the anti-Skp1 immune complex. In contrast, less than 5% of the substrate was conjugated in the absence of Rbx1 by either Cdc53 or Skp1 imnune complexes, despite the presence of larger amounts of Cdc4 or Cdc53. To examine the extent of activation and the concentration dependence of Rbx1 activation, SCF$^{Cdc4}$ complexes were purified from insect cells co-expressing varying levels of MYC-Rxb1 and then assayed for Sic1 ubiquitin conjugating activity. In the absence of Rbx1, low levels of conjugates were observed. Increasing quantities of Rbx1 led to increasing levels of ubiquitination, with the maximal extent of activation approaching 20-fold. This estimate represents a lower limit of the extent to which Rbx1 can increase the rate of accumulation of Sic1-GST-Ub$^{RA}$ conjugates, because a large fraction of the phosphorylated Sic1 substrate was depleted at the end of the reactions. Immunoblot analysis of these complexes revealed that the levels of Cdc53, Cdc4, and Skp1 were constant throughout the Rbx1 titration.

EXAMPLE 2

Use of Rbx1 with SCF$^{\beta-TRCP}$ to Stimulate IκBα Ubiquitination

As another example of utilizing Rbx1 as a research tool, Rbx1 can be used to stimulate ubiquitination of phosphorylated IκB in the presence of E1 ubiquitin-activating enzyme, the E2 ubiquitin conjugation enzyme UBC5C, ATP, GST-Ub$^{RA}$, and SCF$^{\beta-TRCP}$ (which contains the F-box protein β-TRCP). (Yaron, et al. 1998. "Identification of the receptor component of the IκBα-ubiquitin ligase," *Nature* 396:590–594; Winston, et al. 1999. "The SCF$^{\beta-TRCP}$-ubiquitin ligase complex associates specifically with phosphorylated destruction notifs in IκBα and β-catenin and stimulates IκBα ubiquitination in vitro," *Genes Dev* 13:270–283). In a preferred embodiment, complex of Rbx1 and SCF$^{\beta-TRCP}$ can be purified from lysates of Hi5 or Sf21 insect cells infected with baculoviruses encoding SCF subunits and Rbx1. Complexes can be supplemented with phosphorylated IκB prepared as described by Winston (Winston, et al. 1999. *Genes Dev* 13:270–283), UBC5 C, E1 ubiquitin-activating enzyme, ATP, and GST-Ub$^{RA}$. After a period of incubation, reaction products can be subject to SDS-PAGE and analyzed by Western blotting using antibodies against IκBα. Conjugation of GST-Ub$^{RA}$ to IκBα can result in the formation of a ladder of IκBα conjugates differing in size by ~35 kD, the size of GST-Ub$^{RA}$. Confirmation that Rbx1 can be used as a research tool has been published, e.g. Tan et al, *Mol Cell* 3:527 (1999).

EXAMPLE 3

Use of Rbx1 with the VHL Complex to Reconstitute HIF1α Ubiquitination

As another example of utilizing Rbx1 as a research tool, Rbx1 was used in assays for ubqitination of HIF1α (Maxwell et at "The tumor suppressor protein VHL targets hypoxiinducible factors for oxygen-dependent proteolysis" *Nature* 399:271, 1999) in the presence of E1 ubiquitin-activating enzyme, the E2 ubiquitin conjugation enzyme UBC5a, ATP, GST-Ub$^{RA}$, and a complex consisting of VHL protein, Elongin B, Elongin C, CUL2, and Rbx1. In a preferred embodiment, the VHL-containing complex is purified from Sf21 insect cells infected with baculoviruses encoding subunits of the VHL complex. VHL complexes are supplemented with lysates from insect cells infected with baculoviruses encoding HIF1 or HIF2 and with UBC5a, E1 ubiquitin activating enzyme, ATP, and GST-Ub$^{RA}$. After a period of incubation, reaction products are subjected to SDS-PAGE and analyzed by Western blotting using antibodies against HIF1α. Conjugation of GST-Ub$^{RA}$ to HIF1α results in the formation of a ladder of HIF1α conjugates differing in size by ~35 kD, the size of GST-Ub$^{RA}$.

EXAMPLE 4

Use of Rbx1 to Stimulate Rub1 (NEDD8) Modification of Cullin Proteins

Rbx1 was used to stimulate modification of the cullin proteins Cdc53 and CUL2 with the ubiquitin-like protein Rub1 (also known as NEDD8) in the presence of Rub1-activating enzyme Uba3/Ula1, Rub1-conjugating enzyme Ubc12, ATP, GST-Rub1, and a complex consisting of Rbx1 and either Cdc53 or Cul2 (Kamura et al "The Rbx1 subunit of SCF and VHL E3 ubiquitin ligase activates Rub1 modification of cullins Cdc53 and Cul2" *Genes Dev.* 13:2928, 1999). In one embodiment, the Cdc53-Rbx1 complex is purified from Sf21 cells infected with baculoviruses encoding Cdc53 and Rbx1. Complexes are supplemented with Uba3/Ula1, Ubc12, ATP, and GST-Rub1. After a period of incubation, reaction products are subjected to SDS-PAGE and analyzed by Western blotting using antibodies that recognize Cdc53. Conjugation of GST-Rub1 to Cdc53 results in disappearance of ummodified Cdc53 and appearance of a new, more slowly migrating band corresponding to the Cdc53-GST-Rub1 conjugate. In another embodiment, the CUL2-Rbx1 complex is purified from SE21 cells infected with baculoviruses encoding CUL2 and Rbx1. Complexes are supplemented with Uba3/Ula1, Ubc12, ATP, and GST-Rub1. After a period of incubation, reaction products are subjected to SDS-PAGE and analyzed by Western blotting using antibodies that recognze CUL2. Conjugation of GST-Rub1 to CUL2 results in disappearance of unmodified CUL2 and appearance of a new, more slowly migrating band corresponding to the Cdc53-GST-Rub1 conjugate.

EXAMPLE 5

Reconstitution of the VHL Complex

Reconstitution of the VHL complex and its subassemblies in insect cells and with bacterially expressed proteins in vitro shows that Rbx1 can interact with VHL, CUL2, and the Elongin BC complex.

Rbx1 and VHL were subctoned into pBacPAK8 with N-terminal His tags and N-terminal myc and C-terminal FLAG tags, respectively. CUL1 was introduced in to the same vector with a C-terminal HA tag, and CUL2 was introduced into pBacPAK-His1 with N-terminal His and HA tags, and recombinant baculoviruses were generated using the BacPAK baculovirus expression system (Clontech). The baculovirus vectors encoding *S. cerevisiae* CDC53 (Willems, et al. 1996. "Cdc53 targets phosphorylated G1 cyclins for degradation by the ubiquitin proteolytic pathway," *Cell* 86:453–463) and Elongins B and C have been described (Kanura, et al. 1998. "The Elongin BC complex interacts with the conserved SOCS-box motif present in members of the SOCS, ras, WD-40 repeat, and ankyrin repeat FAMILIES," *Genes Dev* 12:3872–3881). Sf21 cells were cultured in Sf-900 II SFM with 5% fetal calf serum at 27° C. and coinfected with various combinations of baculoviruses encoding myc-Rbx1, FLAG-VHL, HA-CUL2, HPC4-Elongin B, and HSV-Elongin C. At 60 hours after infection, Sf21 cells were collected and lysed by gentle vortexing in ice-cold buffer containing 40 mM Hepes-NaOH, pH 7.9, 150 mM NaCl, 1 mM DTT, 0.5% (v/v) glycerol, 5 µg/ml leupeptin, 5 µg/ml antipain, 5 µg/ml pepstatin A, and 5 µg/ml aprotinin. Lysates were centrifuged at 10,000×g for 20 minutes at 4° C. The supernatants were used for immnunoprecipitations.

For the expression and purification of recombinant proteins in *E. coli*, full-length mouse Rbx1 was expressed in pRSET B (Invitrogen) with N-terminal 6-histidine and myc epitope tags. Human VHL was expressed in pRSET B with N-terminal 6-histidine and C-terminal FLAG epitope tags. Purification of recombinant proteins from inclusion bodies and expression constructs for Elongins B and C have been described previously. (Kamura, et al. 1998. *Genes Dev* 12:3872–3881).

The procedures for inmmunoprecipitations and Western Blotting are as follows. Anti-T7 and anti-HSV antibodies were from Novagen. Anti-HA (12CA5) and anti-c-myc (9E10) antibodies were from Boebringer-Mannheim. Anti-FLAG (M2) was from Eastman Kodak. Anti-Elongin C monoclonal antibody was from Transduction Laboratories. Anti-VHL monoclonal antibody (Ig32) was from Pharmingen. Anti-Sic1 (yN-19 and yC-19) and anti-Cdc53 (yC-17) antibodies were from Santa Cruz Biotechnology, Inc. Anti-Elongin B rabbit polyclonal antibodies were described previously. (Garrett, et al. 1995. "Positive regulation of general transcription sm by a tailed ubiquitin homolog," *Proc Natl Acad Sci USA* 92:7172–7176). Anti-HPC4 monoclonal antibody (Stearns, et al. 1988. "The interaction of a Ca$^{2+}$-dependent monoclonal antibody with the protein C activation peptide region. Evidence for obligatory Ca$^{2+}$binding to both antigen and antibody," *J Biol Chem* 263:826–832) was obtained from a colleague. Western blots and imnnunoprecipitations of insect cell lysate and refolded bacterially expressed proteins were performed as described. (Kamura, et al. 1998. *Genes Dev* 12:3872–3881).

Figure 3:
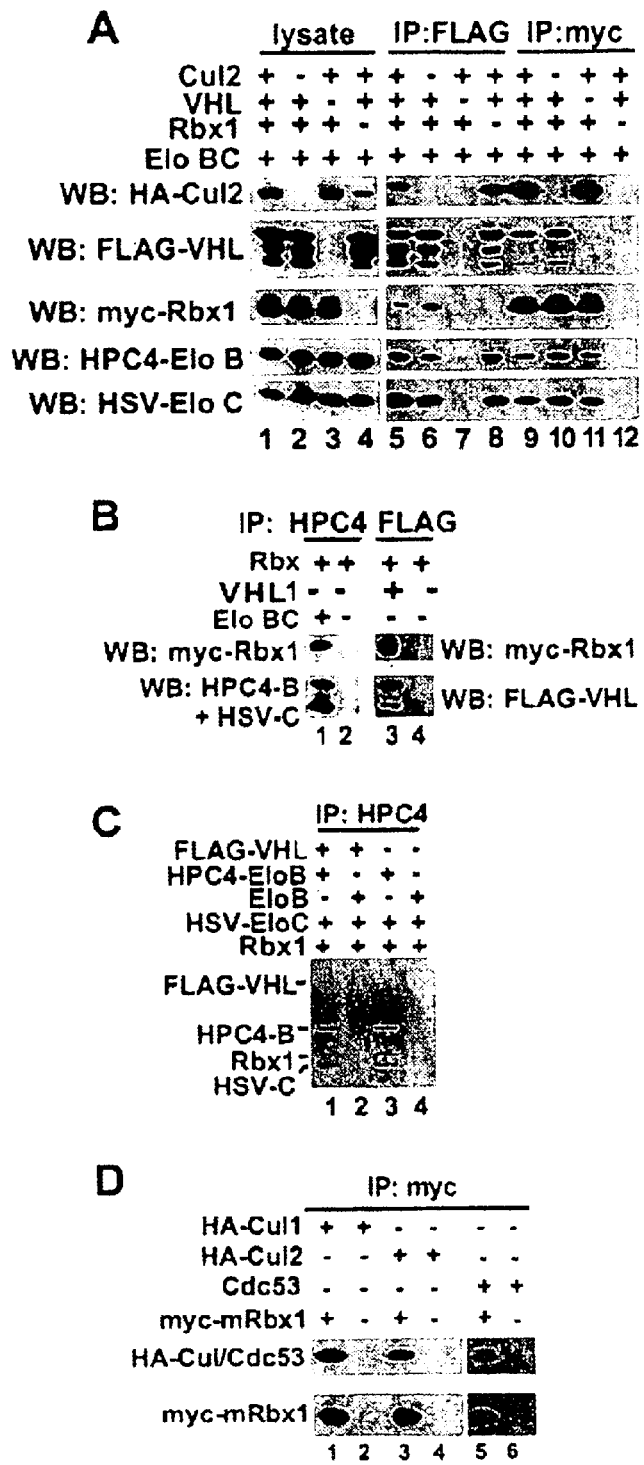
FIGS. 3A–3D depict the reconstitution of Rbx1-containing complexes.

As illustrated in FIG. 3A, all five components of the VHL complex could be coimmunoprecipitated together from Sf21 cell lysates with either anti-FLAG (Lane 5) or anti-myc (Land 9) antibodies. In addition, Rbx1, VHL, and the Elongin CB complex could be coimmunoprecipitated from Sf21 cell lysates with either anti-FLAG (Lane 6) or anti-myc (Lane 10) antibodies in the absence of CUL2; and Rbx1, CUL2, and Elongin BC complex could be coimmuoprecipitated from Sf21 cell lysates with anti-myc antibody in the absence of VHL (Lane 11). As shown in FIGS. 3B and 3D, Rbx1 could also be coimmunoprecipitated with anti-myc antibody with either VHL, CUL2, or the Elongin BC complex from lysates of Sf21 cells coinfected with either myc-Rbx1 and FLAG-VHL, myc-Rbx1 and HA-CUL2, or myc-Rbx1, HPC4-Elongin B, and HSV-Elongin C. Consistent with these results, as shown in FIG. 3C, Rbx1 could be coimmunoprecipitated with VHL-Elongin BC and Elongin BC subassemblies reconstituted in vitro with bacterially expressed FLAG-VHL, HPC4-elongin B, and HSV-Elongin C.

CUL2 is a member of the multiprotein Cullin family (Kipreos, et al. 1996. "Cul-1 is required for cell cycle exit in *C. elegans* and identifies a novel gene family," *Cell* 85:829–839), which also includes the SCF component CUL1 and its *S. cerevisiae* homolog Cdc53. Because Rbx1 interacted with CUL2 as shown in FIG. 3A, the possibility that it might also interact with CUL1 and Cdc53 was examined. As shown in FIG. 3D, Rbx1 binds both human CUL1 and *S. cerevisiae* Cdc53. Myc-Rbx1 and human HA-CUL1 could be coimmunoprecipitated with anti-myc antibodies from lysates of Sf21 cells coinfected with baculoviruses encoding myc-Rbx1 and HA-CUL1. In addition, myc-Rbx1 and Cdc53 could be coimmunoprecipitated with anti-myc antibodies form lysates of Sf21 cells coinfected with baculoviruses encoding myc-Rbx1 and Cdc53.

EXAMPLE 6

Effect of Rbx1 on Function of SCF$^{Cdc4}$ Ubiquitin Ligase

Cdc53/CUL1 is a component of the recently described SCF ubiquitin ligase complex, which catalyzes ubiquitination of a diverse collection of proteins with critical roles in cell cycle, transcription, and development. (Patton, et al. 1998. "Cdc53 is a scaffold protein for multiple Cdc34/Skp1/F-box protein complex that regulate cell division and methionine biosynthesis in yeast," *Genes Dev* 12:692–705; Bai, et al. 1996. "SKP1 connects cell cycle regulators to the ubiquitin proteolysis machinery through a novel motif, the F-box," *Cell* 86:263–274; Patton, et al. 1998. "Combinatorial control in ubiquitin-dependent proteolysis: don't Skp the F-box hypothesis," *Trends Biochem Sci* 14:236–243; Skowyra, et al. 1997. "F-box proteins are receptors that recruit phosphorylated substrates to the SCF ubiquitin-ligase complex," *Cell* 91:209–219; and Feldman, et al. 1997. "A complex of Cdc4p, Skp1p, and Cdc53p/Cullin catalyzes ubiquitination of the phosphorylated CDK inhibitor Sic1p," *Cell* 91:221–230). SCF complexes include Cdc53/CUL1, Skp1, and one of the variety of F-box proteins, which recruit substrates to the SCF for ubiquitination. (Patton, et al. 1998. *Genes Dev* 12:692–705; and Bai, et al. 1996. *Cell* 86:263–274). The results demonstrate that Rbx1 can assemble into complexes containing CUL1 and the additional SCF component Skp1, since Myc-Rbx1 could be co-iunmunoprecipitated with anti-T7 antibodies from lysates of Sf21 cells coinfected with viruses encoding myc-Rbx1, T7-tagged Skp1 (T7-Skp1), and HA-CUL1.

The WD40 repeat protein Cdc4, which recruits the cdk inhibitor Sic1 for ubiquitination by the SCF$^{Cdc4}$ complex, and the leucine-rich repeat protein Grr1, which recruits G1 cyclin Cln2 for ubiquitination by the SCF$^{Grr1}$ complex, are among several F-box proteins found in yeast. Having shown that Rbx1 interacts in cells not only with CUL2 and the VHL complex but also with the SCF components Cdc53/CUL1 (FIG. 3A) and Skp1, mutant yeast strains lacking the chromosomal RBX1 gene were generated in order to test the possibility that Rbx1 might affect functions of SCF$^{Cdc4}$ and SCF$^{Grr1}$.

A *S. cerevisiae* strain lacking the Rbx1 gene was constructed as follows. The Rbx1 gene was disrupted in MCY453 (Mata/MAThis3)-200/his3)-200 can1R/can1R cyh2Rcyh2R ura3/ura3 leu2/leu2 trp1/trp1 lys2/lys2) by replacing the complete Rbx1 ORF (YOL133w) with the HIS3 gene (Baudi et al. 1993. "A simple and efficient method for direct gene deletion in *Saccharomyces cerevisiae.*" *Nucleic Acids Res* 21:3329–3330). For rescue of the rbx1 deletion strain (MCY557) with mammalian RBX1, wild type and mutant mammalian RBX1 genes were fused to the GAL1,10 promoter in the plasmid Yep352-GAL. These plasmids were transformed into MCY557 and URA3+ transformants were selected. Random spores were germinated on galactose medium minus histidine and uracil and allowed to germinate for 4 days at 30° C. The resulting colonies were tested for mating. To confirm that rescue was due to the presence of the SCF4 expression plasmid, cells were tested for the ability to grow in FOA after prolonged growth in medium containing uracil. Sporulation and tetrad dissection showed 2:0 segregation for viability, and all viable spores were HIS⁻, indicating the RBX1 is an essential gene. Inviable spores produced ricrocolonies of 10–20 cells, many of which were abnormally elongated or contained multiple, abnormally shaped buds. *S. cerevisiae* strains containing mutations in genes encoding the SCF components Cdc53, Skp1, Cdc4, and Cdc34 exhibit a similar morphology. This phenotype was due to the RBX1 deletion, because the rbx1 deletion strain could be rescued by expression of yRbx1.

Figure 4:
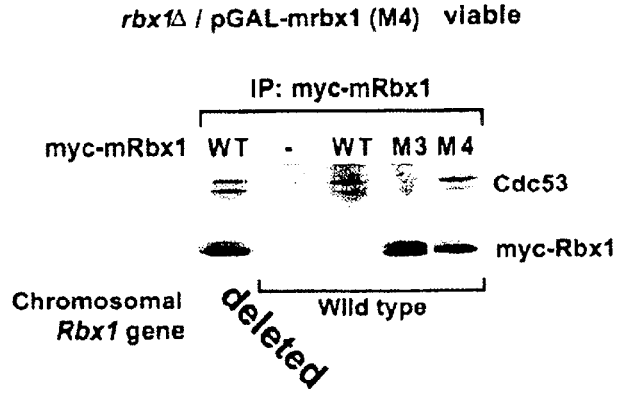
FIGS. 4A–4C depict various activities associated with the presence or absence of Rbx1.
Figure 4:
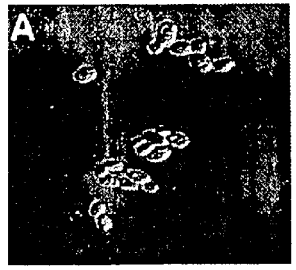
Figure 4:
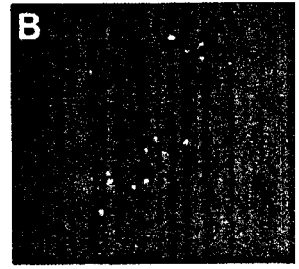
Figure 4:
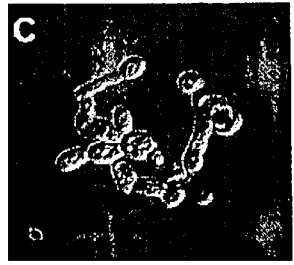
Figure 4:
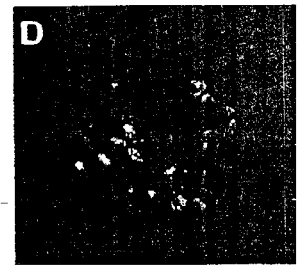

The Rbx1 deletion strain was also rescued by expression of either myc-tagged mammalian Rbx1 (mRbx1) or a mutant mRbx1 (M4), in which putative ring finger cysteine 53 and cysteine 56 were replaced with serines. The rbx1 deletion strain was not rescued, however, by expression of a mutant mRbx1 (M3), in which putative ring finger cysteine 42 and cysteine 45 were replaced by serines. When expressed in either the rbx1 deletion strain or in a wild type background, myc-tagged mRbx1 coimmunoprecipitated with the endogenous yeast Cdc53 protein, suggesting that it associates with Cdc53 in cells (FIG. 4A). Furthermore, coimmunopecipitation of wild type and mutant mRbx1 proteins with Cdc53 correlated with their abilities to rescue the deletion phenotype, since significantly more Cdc53 was coimmunoprecipitated with the complementating mRbx1 M4 mutant than with the noncomplementating M3 mutant (FIG. 4A).

These results show that yeast Rbx1 (yRbx1) is a subunit and activator of the $SCF^{Cdc4}$ ubiquitin ligase and that mammalian Rbx1 (mRbx1) can substitute for its yeast counterpart in reconstitution of the active $SCF^{Cdc4}$ complex.

The $SCF^{Cdc4}$ complex is required for ubiquitination and targeted degradation of a variety of cell cycle regulatory proteins including Sic1, whose degradation is essential for the G1/S transition. The $SCF^{Grr1}$ complex is required for ubiquitination and targeted degradation of the G1 cyclin Cln2. As one means of addressing the role of Rbx1 in these processes, myc-tagged wild type or M4 mutant mRbx1 were expressed in the rbx1 deletion strain on a high copy number plasmid under control of the GAL1,10 promoter. When cells carrying the plasmid were shifted from galactose medium to glucose medium, Rbx1 protein was depleted, and the fraction of cells exhibiting the elongated bud morphology increased dramatically (FIG. 4C). Cells expressing the M4 mutant arrested growth within a few hours of the glucose shift, whereas cells expressing wild type Rbx1 continued to grow slowly, presumably due to the presence of a small amount of residual Rbx1. As expected if M4 cells arrest at least in part due to their inability to ubiquitinate the cell cycle regulators Sic1 and Cln2, M4 cells accumulated Sic1 and Cln2 proteins when shifted into glucose (FIG. 4B).

Showing that Rbx1 is a general subunit of SCF ubiquitin-ligases demonstrates (1) that Rbx1 interacts with subunits of Cdc53/CUL1 containing SCF ubiquitin-ligase complexes, (2) that the abilities of Rbx1 mutants to bind the Cdc53 subunit of SCF ubiquitin ligase correlate with their abilities to prevent cell cycle arrest in a yeast strain lacking chromosomal Rbx1, and (3) that depletion of Rbx1 from yeast interferes with the function of $SCF^{Cdc4}$ and $SCF^{Grr1}$. Having shown that Rbx1 is also a component of the CUL2-containing VHL complex, Rbx1 can now be applied in delineating the function of the VHL complex and perhaps other Cullin complexes as possible ubiquitin ligases and ubiquitin-like ligases for as yet unidentified sets of target proteins. Since the multiprotein VHL complex has been shown to have roles in cell cycle regulation through its control of the levels of the cdk inhibitor p27, in repression of hypoxia-inducible genes, and in assembly of the extracellular fibronectin matrix, Rbx1 can be applied in the reconstitution of VHL complexes to determine therapeutics that cause the dissociation of the VHL complex. Further, Rbx1 is a component of the $SCF^{Cdc4}$ complex, functioning as a common SCF subunit and participating in regulation of ubiquitination by SCF complexes containing additional F-box proteins, including MET30 and β-TRCP, which direct ubiquitination of such target proteins as Swe1 and the transcriptional regulators IκB and β-catenin. Thus, Rbx1 can be applied in determining therapeutics capable of regulating ubiquitination via other SCF complexes.

The present invention relates to a component in VHL tumor suppressor activity found in the majority of sporadic clear cell renal carcinomas as well as autosomal dominant familial cancer syndrome that predisposes affected individuals to a variety of tumors including clear cell renal carcinomas, cerebellar hemangioblastomas and hemangiomas, retinal angiomata, and pheochromocytomas; general repression of hypoxia-inducible genes; and regulation of p27 protein stability and fibronectin matrix assembly. The Ring box proteins described act as a cellular marker useful (1) in detecting a possible predisposition to certain carcinomas, (2) as molecular targets for treating those carcinomas therapeutically, (3) as a target for inhibition by drugs that manipulate the growth of cells, and (4) as a research tool to better understand the various complex mechanisms of cell ubiquitination, binding of certain activator proteins, fibronectin deposition and other aspects of the cellular division process.

While the preferred embodiments are shown to illustrate the invention, numerous changes to the materials and methods can be made by those skilled in the art. All such changes are encompassed within the spirit of the invention as defined by the appended claims.

What is claimed is:

1. An isolated and purified biologically active Ring box protein comprising a polypeptide having an amino acid sequence corresponding to SEQ ID NO:1.

2. A recombinant Ring box protein comprising a polypeptide having an amino acid sequence corresponding to SEQ ID NO:1.

3. The Ring box protein of claim 1, wherein the polypeptide is human.

4. A Ring box protein according to claim 2, wherein the polypeptide is encoded by a nucleic acid comprising the sequence of SEQ ID NO:3.

5. A Ring box protein according to claim 2, prepared by the method of culturing an isolated cell containing an expression vector comprising a nucleic acid molecule comprising the sequence of SEQ ID NO:3 under conditions suitable for expression of the nucleic acid molecule.

6. A protein complex comprising the Ring box protein of claim 1 or claim 2.

7. The protein complex of claim 6, further comprising one or more proteins selected from the group consisting of a cullin protein, a substrate recognition protein, and a linker protein.

8. The protein complex of claim 7 wherein the complex is a ubiquitin ligase protein complex.

9. The protein complex of claim 8 wherein the ubiquitin ligase protein complex is selected from the group consisting of SCF and VHL.

10. The ubiquitin ligase protein complex of claim 8 wherein the cullin protein is selected from the group consisting of Cdc53, Cullin 1, Cullin 2, Cullin 3, Cullin 4A, Cullin 4B, and Cullin 5.

11. The ubiquitin ligase protein complex of claim 8 wherein the substrate recognition protein is selected from the group consisting of β-TRCP, Cdc4, Grr1, VHL and Elongin C binding proteins.

12. The ubiquitin ligase protein complex of claim 8 wherein the linker protein is selected from the group consisting of Skp 1 and Elongin C.

* * * * *

SEQUENCE LISTING

<160> NUMBER OF SEQ ID NOS: 12

<210> SEQ ID NO 1
<211> LENGTH: 108
<212> TYPE: PRT
<213> ORGANISM: Homo sapiens
<220> FEATURE:
<223> OTHER INFORMATION: human ring box protein 1 (Rbx1)

```
<400> SEQUENCE: 1

Met Ala Ala Ala Met Asp Val Asp Thr Pro Ser Gly Thr Asn Ser Gly
 1               5                  10                  15

Ala Gly Lys Lys Arg Phe Glu Val Lys Lys Trp Asn Ala Val Ala Leu
            20                  25                  30

Trp Ala Trp Asp Ile Val Val Asp Asn Cys Ala Ile Cys Arg Asn His
        35                  40                  45

Ile Met Asp Leu Cys Ile Glu Cys Gln Ala Asn Gln Ala Ser Ala Thr
    50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Glu Phe Gln Lys Tyr Gly His
            100                 105

<210> SEQ ID NO 2
<211> LENGTH: 121
<212> TYPE: PRT
<213> ORGANISM: Saccharomyces cerevisiae
<220> FEATURE:
<223> OTHER INFORMATION: yeast ring box protein 1 (Rbx1)

<400> SEQUENCE: 2

Met Ser Asn Glu Val Asp Arg Met Asp Val Asp Glu Asp Ser Gln
 1               5                  10                  15

Asn Ile Ala Gln Ser Ser Asn Gln Ser Ala Pro Val Glu Thr Lys Lys
            20                  25                  30

Lys Arg Phe Glu Ile Lys Lys Trp Thr Ala Val Ala Phe Trp Ser Trp
        35                  40                  45

Asp Ile Ala Val Asp Asn Cys Ala Ile Cys Arg Asn His Ile Met Glu
    50                  55                  60

Pro Cys Ile Glu Cys Gln Pro Lys Ala Met Thr Asp Thr Asp Asn Glu
65                  70                  75                  80

Cys Val Ala Ala Trp Gly Val Cys Asn His Ala Phe His Leu His Cys
                85                  90                  95

Ile Asn Lys Trp Ile Lys Thr Arg Asp Ala Cys Pro Leu Asp Asn Gln
            100                 105                 110

Pro Trp Gln Leu Ala Arg Cys Gly Arg
        115                 120

<210> SEQ ID NO 3
<211> LENGTH: 508
<212> TYPE: DNA
<213> ORGANISM: Homo sapiens
<220> FEATURE:
<221> NAME/KEY: CDS
<222> LOCATION: (7)..(333)
<223> OTHER INFORMATION: Rbx1

<400> SEQUENCE: 3
cccaaaatgg cggcagcgat ggatgtggat accccgagcg gcaccaacag cggcgcgggc      60
aagaagcgct ttgaagtgaa aaagtggaat gcagtagccc tctgggcctg ggatattgtg     120
gttgataact gtgccatctg caggaaccac attatggatc tttgcataga atgtcaagct     180
aaccaggcgt ccgctacttc agaagagtgt actgtcgcat ggggagtctg taaccatgct     240
tttcacttcc actgcatctc tcgctggctc aaaacacgac aggtgtgtcc attggacaac     300
```

| agagagtggg aattccaaaa gtatgggcac taggaaaaga cttcttccat caagcttaat | 360 |
| tgttttgtta ttcatttaat tgactttccc tgctgttacc taattacaaa ttggatggaa | 420 |
| ctgtgttttt ttctgctttg ttttttcagt ttgctgtttc tgtagccata ttgtattctg | 480 |
| tgtcaaataa agtccagttg gattctgg | 508 |

<210> SEQ ID NO 4
<211> LENGTH: 480
<212> TYPE: DNA
<213> ORGANISM: Saccharomyces cerevisiae
<220> FEATURE:
<221> NAME/KEY: CDS
<222> LOCATION: (4)..(369)
<223> OTHER INFORMATION: Rbx1

<400> SEQUENCE: 4

| aacatgagca acgaagttga caggatggat gttgatgaag atgaatcgca aaatattgcg | 60 |
| caaagctcaa accaaagtgc gccagtggaa accaaaaaga agagatttga aattaagaaa | 120 |
| tggaccgcag tggcgttttg gtcatgggat atagctgttg acaactgtgc tatttgcagg | 180 |
| aaccatataa tggaaccatg cattgaatgc agccaaagg ccatgacgga cactgataat | 240 |
| gaatgtgtag cagcctgggg tgtctgtaat cacgctttcc atttgcactg tattaataaa | 300 |
| tggatcaaga caagagacgc atgcccatta gataaccaac cttggcagtt agcaagatgc | 360 |
| ggtaggtgaa aaaatgaatt gcccgtaaac atttaaatca taccgaggta gaaggattat | 420 |
| ggcatgttcc tttttttta gagtatgtca actggcgcag tagatacatg tttttctctt | 480 |

<210> SEQ ID NO 5
<211> LENGTH: 504
<212> TYPE: DNA
<213> ORGANISM: Mus sp.
<220> FEATURE:
<221> NAME/KEY: CDS
<222> LOCATION: (18)..(344)
<223> OTHER INFORMATION: Rbx1

<400> SEQUENCE: 5

| gactgtgtgt ttccaaaatg gcggcggcga tggatgtgga tacccccagc ggcaccaaca | 60 |
| gcggcgcggg caagaagcgc tttgaagtta aaaagtggaa tgcagtggcc ctctgggcct | 120 |
| gggacattgt ggttgataac tgtgccatct gcaggaacca cattatggat ctttgtatcg | 180 |
| aatgtcaggc caaccaggcg tcagctactt ccgaagagtg tacggttgca tggggagtct | 240 |
| gcaaccatgc ttttcatttc cactgcatct ctcgatggct caaaacgagg caggtgtgtc | 300 |
| cgttggacaa cagagagtgg gagttccaga agtatgggca ttaggaaaga tttcccgcaa | 360 |
| ggcgtaccca tctgttactt gtctagtgac ttcctgttaa ttatacatta gatagaacca | 420 |
| tggtcctttt tcgttccttt gtttttggag tttggtgttc ccgcagccat attgtatttt | 480 |
| gtgtaaataa agcctttaag ttgg | 504 |

<210> SEQ ID NO 6
<211> LENGTH: 108
<212> TYPE: PRT
<213> ORGANISM: Drosophila melanogaster
<220> FEATURE:
<223> OTHER INFORMATION: Drosophila melanogaster ring box protein 1
      (Rbx1)

```
<400> SEQUENCE: 6

Met Glu Val Asp Glu Asp Gly Tyr Glu Val Pro Ser Ser Ser Ser Lys
1               5                   10                  15

Gly Asp Lys Lys Arg Phe Glu Val Lys Lys Trp Asn Ala Val Ala Leu
                20                  25                  30

Trp Ala Trp Asp Ile Val Val Asp Asn Cys Ala Ile Cys Arg Asn His
            35                  40                  45

Ile Met Asp Leu Cys Ile Glu Cys Gln Ala Asn Gln Ala Ser Ala Thr
        50                  55                  60

Ser Glu Glu Cys Thr Val Ala Trp Gly Val Cys Asn His Ala Phe His
65                  70                  75                  80

Phe His Cys Ile Ser Arg Trp Leu Lys Thr Arg Gln Val Cys Pro Leu
                85                  90                  95

Asp Asn Arg Glu Trp Asp Phe Gln Lys Tyr Gly His
            100                 105

<210> SEQ ID NO 7
<211> LENGTH: 110
<212> TYPE: PRT
<213> ORGANISM: Caenorhabditis elegans
<220> FEATURE:
<223> OTHER INFORMATION: Caenorhabditis elegans ring box protein 1
      (Rbx1)

<400> SEQUENCE: 7

Met Ala Gln Ala Ser Asp Ser Thr Ala Met Glu Val Glu Ala Thr
1               5                   10                  15

Asn Gln Thr Val Lys Lys Arg Phe Glu Val Lys Lys Trp Ser Ala Val
                20                  25                  30

Ala Leu Trp Ala Trp Asp Ile Gln Val Asp Asn Cys Ala Ile Cys Arg
            35                  40                  45

Asn His Ile Met Asp Leu Cys Ile Glu Cys Gln Ala Asn Gln Ala Ala
        50                  55                  60

Gly Leu Lys Asp Glu Cys Thr Val Ala Trp Gly Asn Cys Asn His Ala
65                  70                  75                  80

Phe His Phe His Cys Ile Ser Arg Trp Leu Lys Thr Arg Gln Val Cys
                85                  90                  95

Pro Leu Asp Asn Arg Glu Trp Glu Phe Gln Lys Tyr Gly His
            100                 105                 110

<210> SEQ ID NO 8
<211> LENGTH: 18
<212> TYPE: PRT
<213> ORGANISM: Saccharomyces cerevisiae
<220> FEATURE:
<223> OTHER INFORMATION: Anaphase-Promoting Complex subunit APC11
      sequence

<400> SEQUENCE: 8

Met Lys Val Lys Ile Asn Glu Val His Ser Val Phe Ala Trp Ser Trp
1               5                   10                  15

His Ile

<210> SEQ ID NO 9
<211> LENGTH: 69
<212> TYPE: PRT
<213> ORGANISM: Saccharomyces cerevisiae
<220> FEATURE:
<223> OTHER INFORMATION: Anaphase-Promoting Complex subunit APC11
      sequence
```

-continued

```
<400> SEQUENCE: 9

Asp Glu Asp Val Cys Gly Ile Cys Arg Ala Ser Tyr Asn Gly Thr Cys
1               5                   10                  15

Pro Ser Cys Lys Phe Pro Gly Asp Gln Cys Pro Leu Val Ile Gly Leu
                20                  25                  30

Cys His His Asn Phe His Asp His Cys Ile Tyr Arg Trp Leu Asp Thr
            35                  40                  45

Pro Thr Ser Lys Gly Leu Cys Pro Met Cys Arg Gln Thr Phe Gln Leu
        50                  55                  60

Gln Lys Gly Leu Ala
 65

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence:von
      Hippel-Lindau (VHL) tumor suppressor complex
      tryptic peptide

<400> SEQUENCE: 10

Asn His Ile Met Asp Leu Cys Ile Glu Cys Gln Ala Asn
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence:von
      Hippel-Lindau (VHL) tumor suppressor complex
      tryptic peptide

<400> SEQUENCE: 11

Gln Val Cys Pro Leu Asp Asn Arg Glu Trp Glu Phe Gln Lys
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:von
      Hippel-Lindau (VHL) tumor suppressor complex
      tryptic peptide

<400> SEQUENCE: 12

Trp Asn Ala Val Ala Leu
1               5
```